(12) United States Patent
Wang et al.

(10) Patent No.: US 8,367,827 B2
(45) Date of Patent: Feb. 5, 2013

(54) PROCESS FOR PREPARING HYDROCODONE USING A SUPER ACID

(75) Inventors: Peter X. Wang, Clarkson Valley, MO (US); Tao Jiang, St. Louis, MO (US); Subo Liao, Ballwin, MO (US); Erin Moore, Imperial, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 438 days.

(21) Appl. No.: 12/627,355

(22) Filed: Nov. 30, 2009

(65) Prior Publication Data

US 2010/0137598 A1 Jun. 3, 2010

Related U.S. Application Data

(60) Provisional application No. 61/119,064, filed on Dec. 2, 2008.

(51) Int. Cl.
*C07D 489/02* (2006.01)
*C07D 221/22* (2006.01)
(52) U.S. Cl. .......................................... 546/45; 546/74
(58) Field of Classification Search .................... 546/45, 546/44, 74
See application file for complete search history.

(56) References Cited

FOREIGN PATENT DOCUMENTS

| GB | 2 392 670 | 3/2004 |
|---|---|---|
| WO | WO 2004/022564 A2 | 3/2004 |
| WO | WO 2009/078987 A1 | 6/2009 |

OTHER PUBLICATIONS

Iijima et al., "Studies in the (+_-Morphinan Series. 4. A Markedly Improved Synthesis of (+)-Morphine", Journal of Organic Chemistry, American Chemical Society, 43(7), 1978, pp. 1462-1463; XP 001156547.

Glates et al., "The Closure of the Oxide Bridge in the Morphine Series", Journal of the American Chemical Society, 84, 1962, pp. 4125-4130, XP 002568532.

Goto et al., "Studies on Sinomenine. LX. On the Dehydration of Dihydrosinomeninone and (+) Demethoxy . . . ", Acta Phytochimica, vol. XV, No. 2, 1949, pp. 187-191.

Iijima et al., "Studies in the (+)-Morphinan Series . . . ", J. Org. Chem., vol. 43, No. 7, 1978, pp. 1462-1463.

*Primary Examiner* — Charanjit Aulakh

(57) ABSTRACT

The present disclosure generally relates to a process for converting a fused, tricyclic compound to a fused, tetracyclic compound that includes a furan ring therein. More particularly, the present disclosure related to a process for preparing a hydrocodone compound, or a compound structurally related thereto, and in particular (+)-hydrocodone, by subjecting a structurally corresponding sinomenine starting compound to a super acid-assisted furan ring closure reaction.

24 Claims, No Drawings

PROCESS FOR PREPARING HYDROCODONE USING A SUPER ACID

CROSS REFERENCE TO RELATED APPLICATIONS

This application claims the benefit of U.S. Provisional Application No. 61/119,064 filed Dec. 2, 2008 which is hereby incorporated by reference in its entirety.

FIELD OF THE DISCLOSURE

The present disclosure generally relates to a process for converting a fused, tricyclic compound to a fused, tetracyclic compound that includes a furan ring therein. More particularly, the present disclosure related to a process for preparing a hydrocodone compound, or a compound structurally related thereto, and in particular (+)-hydrocodone, by subjecting a structurally corresponding sinomenine starting compound to a super acid-assisted furan ring closure reaction.

BACKGROUND OF THE DISCLOSURE (+)-Hydrocodone is an opioid with utility as a pharmaceutical compound because of its analgesic properties. Furthermore, (+)-hydrocodone is a key intermediate in the synthesis of other opioids, and in particular unnatural (+)-opioids such as (+)-morphine that have known pharmacological effects (e.g., low micro-molar affinity for the site of the N-methyl-D-aspartate (NMDA) receptor in the rat forebrain, and suggested clinical potential in the treatment of neuropathic pain). (See, e.g., Neuroscience Letters 295 (2000), 21-24.) (+)-Hydrocodone may have significant therapeutic potential if used alone, or if used in combination with other drugs to treat pain, inflammation, cancer, immune disorders, and other diseases.

(+)-Hydrocodone, as illustrated by the structure below, has a fused, tetracyclic core ring structure that includes a furan ring.

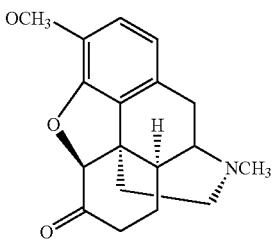

It can be prepared by processes that include subjecting dihydrosinomenine or dihydrosinomeninone, both of which as illustrated below include a fused, tricyclic core ring structure, to a furan ring closure or ring formation reaction.

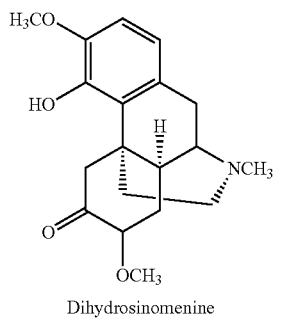
Dihydrosinomenine

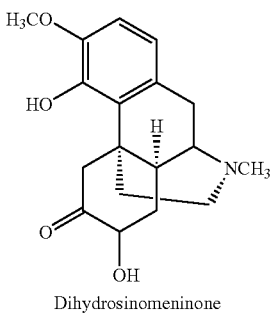
Dihydrosinomeninone

However, current methods of converting dihydrosinomenine to (+)-hydrocodone typically involve the use of large excesses of polyphosphoric acid or a mixture of methanesulfonic acid and phosphorus pentoxide, while current methods of converting dihydrosinomeninone to (+)-hydrocodone typically involve the use of harsh reaction conditions (e.g., boiling dihydrosinomeninone in 50% sulfuric acid). (See, e.g., Goto, K. et al., Acta Phytochim. (Japan), 1949, 15, 187-191; Lijuma, I. et al., C. J. Org. Chem., 1978, 43(7), 1462-1463; and/or, Whittall, J. et al., UK Patent Application No. GB2392670A.)

The currently employed processes for synthesizing (+)-hydrocodone are undesirable for a number of reasons. For example, one or more of these processes may suffer from inefficiency because of the need for a large amount of base to quench the excessive amount of acid used in the reaction, and/or because of the large amount of energy needed to boil the reaction mixture. Such processes may therefore be difficult and expensive to scale up.

In view of the foregoing, a need continues to exist for an improved process for preparing (+)-hydrocodone, as well as other compounds structurally related thereto.

SUMMARY OF THE DISCLOSURE

Briefly, therefore, the present disclosure is generally directed to a process for carrying out a furan ring closure or furan ring formation reaction to transform a fused, tricyclic ring structure, and in particular the compound of Formula (I), to a fused, hetero-tetracyclic ring structure, and in particular the compound of Formula (II), as illustrated in Reaction Scheme 1, below:

Reaction Scheme 1

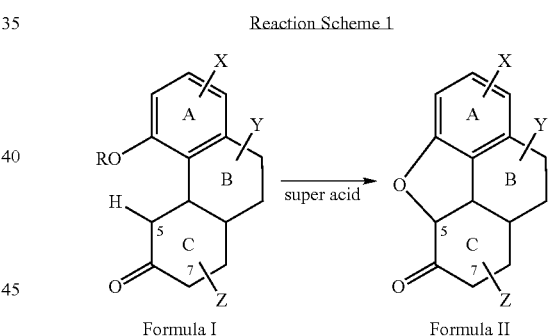

Formula I          Formula II wherein: R is selected from the group consisting of hydrogen or an oxygen-protecting group that may be removed by acid hydrolysis, such as for example acyl, trialkylsilyl, tertiary-alkyl, aryl-substituted methyl, and alkoxy-carbonyl (i.e., $R_aOCO$—, wherein $R_a$ is alkyl as defined elsewhere herein); X generally represents 3 substituents on the A ring, which may be the same or different and which may be independently selected from hydrogen, halogen, alkoxy (i.e., —$OR_b$, wherein $R_b$, is alkyl, as defined elsewhere herein), cyano, hydrocarbyl, substituted hydrocarbyl and $NR_cR_d$, where each of $R_c$ and $R_d$ are independently selected from the group consisting of hydrogen, hydroxy and hydrocarbyl; Y generally represents 5 or 6 substituents on the B ring, which may be the same or different and which may be independently selected from hydrogen, hydrocarbyl, substituted hydrocarbyl, heterohydrocarbyl, and substituted heterohydrocarbyl, with the proviso that when Y represents 5 substituents, at least one of the substituents forms a bridge between two carbon atoms in the B ring; and, Z generally represents between 3 and 5 substituents on the C ring, which may be the same or different and which may be independently selected from H, hydroxy, hydrocarbyl, substituted hydrocarbyl, heterohydrocarbyl (e.g., alkoxy, such as methoxy), and substituted heterohydrocarbyl (e.g., substituted alkoxy, such as substituted methoxy), with the provisos that (i) at least one of the Z substituents is hydroxy or alkoxy at either the C5 or C7 position on the C ring, and (ii) when Z represents 3 substituents, the C ring includes a carbon-carbon double bond therein. The process comprises contacting the compound of Formula (I) with a super acid under process conditions suitable for forming a bond between the oxygen of the —OR substituent of the A ring and a carbon atom of the C ring, such that a furan ring is formed.

More particularly, however, the present disclosure is directed to such process for conversion of a compound of Formula (III) to a compound of Formula (IV) which comprises contacting the compound of formula (III) with a super acid, as shown in Reaction Scheme 2, below:

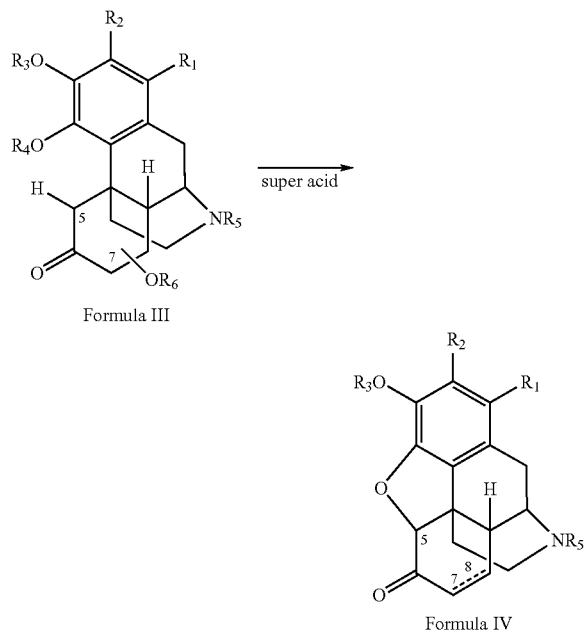

Reaction Scheme 2

Formula III

Formula IV wherein: $R_1$ and $R_2$ are independently selected from the group consisting of hydrogen, halogen, alkoxy (i.e., —$OR_b$, wherein $R_b$ is alkyl, as defined elsewhere herein), cyano, hydrocarbyl, substituted hydrocarbyl and $NR_cR_d$, where each of $R_c$ and $R_d$ are independently selected from the group consisting of hydrogen, hydroxy and hydrocarbyl; $R_3$ and $R_5$ are independently selected from the group consisting of hydrogen, hydrocarbyl and substituted hydrocarbyl; $R_4$ is selected from the group consisting of hydrogen, acyl, trialkylsilyl, tertiary-alkyl, aryl-substituted methyl, and alkoxy-carbonyl (i.e., $R_aOCO$—, wherein $R_a$ is alkyl as defined elsewhere herein); and $R_6$ is a substituent at C5 or C7 and is selected from hydrogen, alkyl, and acyl; and, further wherein a carbon-carbon double bond may optionally be formed (denoted by the dashed bond therein). In the process, a bond is formed between the oxygen atom of —$OR_4$ substituent of the A ring and a carbon atom (i.e., the C5 carbon atom) of the C ring, such that a furan ring is formed.

Still more particularly, and in accordance with Reaction Scheme 3A below, the present disclosure is directed to a process for preparing a compound of Formula VI, and in one particularly preferred embodiment (+)-hydrocodone. The process comprises contacting dihydrosinomenine, which has the structure of Formula V, with a super acid, and preferably a solution comprising a super acid selected from the group consisting of $CF_3SO_3H$, $HBF_4$, $HPF_6$, $FSO_3H$, $HSbF_6$, $FP(O)(OH)_2$ and combinations thereof, to obtain the compound of Formula VI:

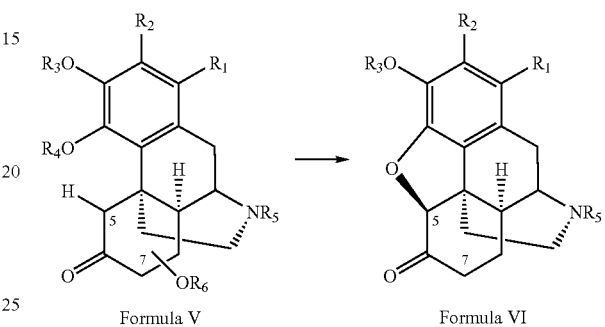

Reaction Scheme 3A

Formula V

Formula VI wherein: $R_1$, $R_2$, $R_3$, $R_4$ and $R_5$ are as previously defined, and in one particular embodiment are H, H, $CH_3$, H, and $CH_3$, respectively, and further wherein $OR_6$ is a substituent at the C5 or C7 position and $R_6$ is H or $CH_3$. In the process, a bond is formed between the oxygen atom of —$OR_4$ substituent of the A ring and a carbon atom (i.e., the C5 carbon atom) of the C ring, such that a furan ring is formed.

In an alternative embodiment to the foregoing, and in accordance with Reaction Scheme 3B below, the present disclosure is directed to a process for preparing a compound of Formula VIII. The process comprises contacting the compound of Formula VII with a super acid, and preferably a solution comprising a super acid selected from the group consisting of $CF_3SO_3H$, $HBF_4$, $HPF_6$, $FSO_3H$, $HSbF_6$, $FP(O)(OH)_2$ and combinations thereof, to obtain the compound of Formula VIII:

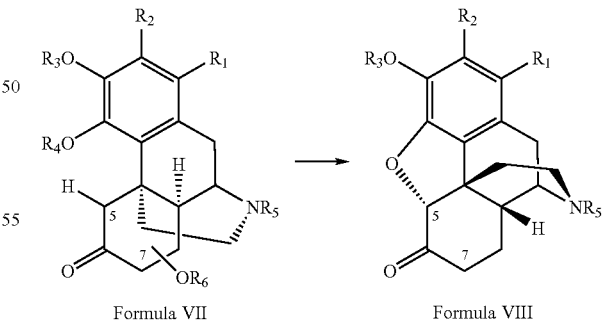

Reaction Scheme 3B

Formula VII

Formula VIII wherein: $R_1$, $R_2$, $R_3$, $R_4$ and $R_5$ are as previously defined, and in one particular embodiment are H, H, $CH_3$, H, and $CH_3$, respectively, and further wherein $OR_6$ is a substituent at the C5 or C7 position and $R_6$ is H or $CH_3$. In the process, a bond is formed between the oxygen atom of —$OR_4$ substituent of the A ring and a carbon atom (i.e., the C5 carbon atom) of the C ring, such that a furan ring is formed.

Additionally, the present disclosure is further directed to the compound obtained from one or more of the foregoing processes. In particular, the present disclosure is further directed to the compound (+)-hydrocodone, prepared by the present process.

Other features and embodiments will be in part apparent from the foregoing, and in part pointed out further below.

DETAILED DESCRIPTION OF THE DISCLOSURE

In accordance with the present disclosure, and as further detailed in Reaction Scheme 1 below, it has been discovered that, under suitable reaction conditions, a super acid may be used to achieve a furan ring closure or furan ring formation, such that a fused, tricyclic ring structure, and in particular the compound of Formula (I), may be transformed into a fused, hetero-tetracyclic ring structure, and in particular the compound of Formula (II):

Reaction Scheme 1

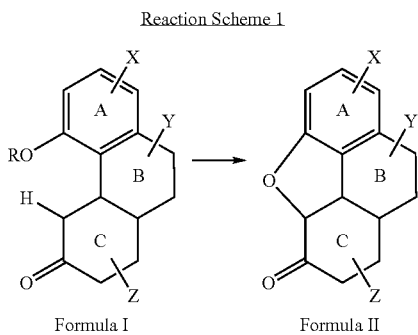

Formula I     Formula II wherein: R is selected from the group consisting of hydrogen or an oxygen-protecting group that may be removed by acid hydrolysis, such as for example acyl, trialkylsilyl, tertiary-alkyl, aryl-substituted methyl, and alkoxy-carbonyl (i.e., $R_aOCO-$, wherein $R_a$ is alkyl as defined elsewhere herein); X generally represents 3 substituents on the A ring, which may be the same or different and which may be independently selected from hydrogen, halogen, alkoxy (i.e., $-OR_b$, wherein $R_b$ is alkyl, as defined elsewhere herein), cyano, hydrocarbyl, substituted hydrocarbyl and $NR_cR_d$, where each of $R_c$ and $R_d$ are independently selected from the group consisting of hydrogen, hydroxy and hydrocarbyl; Y generally represents 5 or 6 substituents on the B ring, which may be the same or different and which may be independently selected from hydrogen, hydrocarbyl, substituted hydrocarbyl, heterohydrocarbyl, and substituted heterohydrocarbyl, with the proviso that when Y represents 5 substituents, at least one of the substituents forms a bridge between two carbon atoms in the B ring (the bridging moiety being a heterohydrocarbyl moiety, particularly an aminoalkyl moiety, and even more particularly an aminoethyl moiety); and, Z generally represents between 3 and 5 substituents on the C ring, which may be the same or different and which may be independently selected from H, hydroxy, hydrocarbyl, substituted hydrocarbyl, heterohydrocarbyl (e.g., alkoxy, such as methoxy), and substituted heterohydrocarbyl (e.g., substituted alkoxy, such as substituted methoxy, ethoxy, etc.), with the provisos that (i) at least one of the Z substituents is hydroxy or alkoxy (e.g., methoxy, ethoxy, etc.) at either the C5 or C7 position on the C ring, and (ii) when Z represents 3 substituents, the C ring includes a carbon-carbon double bond therein. Advantageously, such a furan ring closure reaction may be carried out using mild reaction conditions (e.g., lower reaction temperature), as compared to conventional or existing processes.

In this regard it is to be noted that, as used herein, the term "super acid" refers to an acid having an acidity greater than that of 100% sulfuric acid, as determined using means generally known in the art. In particular, super acids may be characterized as acids having a Hammett acidity function ($H_0$) that is less (i.e., more negative) than that of 100% sulfuric acid, which has an ($H_0$) of −12. Examples of super acids useful in the processes described herein include, but are not limited to, trifluoromethanesulfonic acid ($CF_3SO_3H$), tetrafluoroboric acid ($HBF_4$), fluorophosphoric acid ($HPF_6$), fluorosulfuric acid ($FSO_3H$), and fluoroantimonic acid ($HSbF_6$), fluorophosphoric acid ($FP(O)(OH)_2$) as well as combinations thereof. These acids, and other super acids, may be obtained commercially, for example, from Sigma-Aldrich. Additionally, or alternatively, the super acids may optionally be formed in situ using means generally known in the art, such as for example by the reaction of either water or methanol with a reagent such as an anhydride of the desired super acid, including for example trifluoromethanesulfonic anhydride and fluorosulfonic anhydride which also may be obtained commercially.

Although the process of the present disclosure may be generally used as detailed above in Reaction Scheme 1, wherein a bond is formed between the oxygen atom of the —OR substituent on the A ring and a carbon atom (the C5 carbon, as further detailed elsewhere herein) on the C ring, in a more preferred embodiment the process of the present disclosure may comprise contacting a compound of Formula (III) with a super acid, as illustrated in Reaction Scheme 2 below, to obtain a compound of Formula (IV):

Reaction Scheme 2

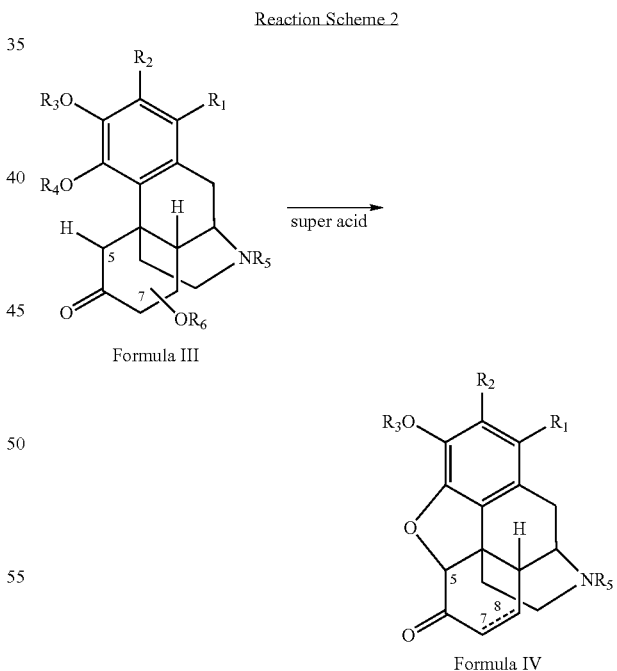

Formula III

Formula IV wherein: $R_1$ and $R_2$ are independently selected from the group consisting of hydrogen, halogen, alkoxy (i.e., $-OR_b$, wherein $R_b$ is alkyl, as defined elsewhere herein), cyano, hydrocarbyl, substituted hydrocarbyl and $NR_cR_d$, where each of $R_c$ and $R_d$ are independently selected from the group consisting of hydrogen, hydroxy and hydrocarbyl; $R_3$ and $R_5$ are independently selected from the group consisting of hydrogen, hydrocarbyl and substituted hydrocarbyl; $R_4$ is selected from the group consisting of hydrogen, acyl, trialkylsilyl, tertiary-alkyl, aryl-substituted methyl, and alkoxy-carbonyl (i.e., $R_aOCO—$, wherein $R_a$ is alkyl as defined elsewhere herein); and $R_6$ is a substituent at C5 or C7 and is selected from hydrogen, alkyl, and acyl. Particularly preferred embodiments include those wherein $R_1$ and $R_2$ are independently selected from the group consisting of hydrogen and lower alkyl (e.g., $C_1$-$C_4$ alkyl); and/or $R_4$ is hydrogen; and/or $R_3$ is hydrogen or hydrocarbyl, and more particularly is hydrogen or lower alkyl (e.g., $C_1$-$C_4$ alkyl), and still more particularly is hydrogen or methyl; and/or $R_5$ is hydrogen or substituted or unsubstituted hydrocarbyl, and more particularly is hydrogen or lower alkyl (e.g., $C_1$-$C_4$ alkyl), and still more particularly is hydrogen or methyl; and/or $R_6$ is hydrogen or substituted or unsubstituted hydrocarbyl, and more particularly is hydrogen or lower alkyl (e.g., $C_1$-$C_4$ alkyl), and still more particularly is methyl. In the reaction, a bond is formed between the oxygen atom of the $—OR_4$ substituent on the A ring and a carbon atom of the C ring, and in particular the C5 carbon atom of the C ring (as further detailed elsewhere herein below).

In this regard it is to be noted that, in one particular preferred embodiment, the process may result in the formation of a carbon-carbon double bond in the compound of Formula IV (denoted by the dashed bond therein between carbon atoms C7 and C8, the numbering of the carbon atoms in the structure being further detailed elsewhere herein below). Other particularly preferred embodiments are described in Table 1, below, wherein the substituents corresponding to each of the R groups are identified, and further wherein each row represents a specific embodiment of the disclosure.

TABLE 1

| Compound | R1 | R2 | R3 | R4 | R5 | R6 |
|---|---|---|---|---|---|---|
| A | H | Br | $CH_3$ | H | $CH_3$ | $CH_3$ |
| B | H | H | $CH_3$ | H | cyclopropylmethyl | $CH_3$ |
| C | H | H | $CH_3$ | H | H | $CH_3$ |
| D | H | H | H | H | $CH_3$ | OH |
| E | H | H | $CH_3$ | H | $CH_3$ | $CH_3$ |

Additionally, and in further accordance with the present disclosure, the present process may be carried out so as to ensure the stereochemistry at one or more chiral carbon atoms present in the starting compound is maintained. For example, in one particularly preferred embodiment, the compound of Formula (V) may be contacted with a super acid to form the compound of Formula (VI), as illustrated in Reaction Scheme 3A, below:

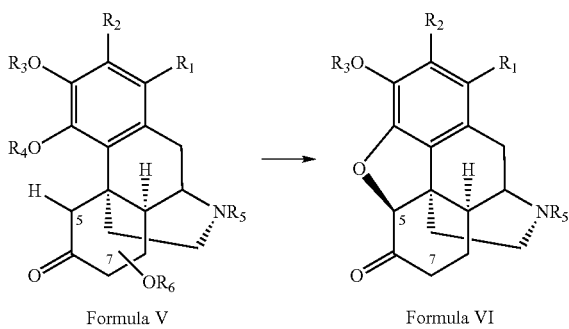

Reaction Scheme 3A

Formula V       Formula VI wherein: $R_1$, $R_2$, $R_3$, $R_4$ and $R_5$ are as previously defined, and in one particular embodiment are H, H, $CH_3$, H, and $CH_3$, respectively, and further wherein $OR_6$ is a substituent at the C5 or C7 position and $R_6$ is H or $CH_3$. In one particularly preferred embodiment, however, the compound of Formula (VI) is (+)-hydrocodone; that is, in one particularly preferred embodiment $R_1$, $R_2$ and $R_4$ are H, while and $R_3$ and $R_5$ are $CH_3$.

In an alternative embodiment to the one illustrated above, the compound of Formula (VII) may be contacted with a super acid to form the compound of Formula (VIII), as illustrated in Reaction Scheme 3A, below:

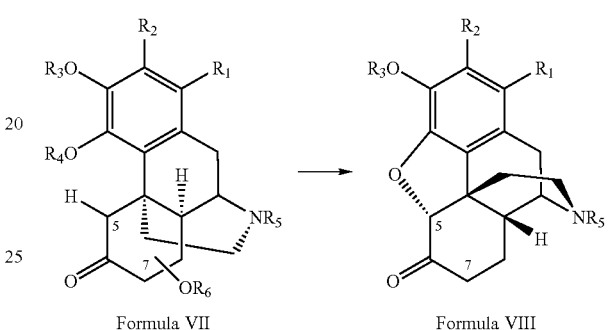

Reaction Scheme 3B

Formula VII       Formula VIII wherein: $R_1$, $R_2$, $R_3$, $R_4$ and $R_5$ are as previously defined, and in one particular embodiment are H, H, $CH_3$, H, and $CH_3$, respectively, and further wherein $OR_6$ is a substituent at the C5 or C7 position and $R_6$ is H or $CH_3$.

One or more of the reactions of the present disclosure, as illustrated above, may be carried with or without the use of a solvent and in solution or suspension, the starting compound (i.e., the compound of Formula I, III, V or VII) and/or the super acid, and/or other reagents being dissolved or suspended therein. Preferably, however, the reaction is carried out in the presence of a solvent, and in particular an aprotic solvent. Suitable solvents include, but are not limited to, chloroform, dichloromethane, chlorobenzene, toluene, dichloroethane, tetrahydrofuran, diethyl ether, and acetonitrile, among others, as well as combinations thereof.

In addition to the super acid, as defined above, the reaction solution or mixture may optionally comprise one or more secondary acids that are not super acids. Suitable examples of such additional acids include, but are not limited to, methanesulfonic acid ($MeSO_3H$), phosphoric acid ($H_3PO_4$), toluenesulfonic acid ($CH_3C_6H_4SO_3H$), and trifluoromethanecarboxylic acid ($CF_3CO_2H$), as well as combinations thereof. The reaction solution may also optionally comprise one or more anhydrides. Suitable examples of anhydrides that may be used in accordance with the present disclosure include, but are not limited to, methanesulfonic anhydride, toluenesulfonic anhydride, trifluoroacetic anhydride and phosphorous pentoxide ($P_2O_5$), as well as combinations thereof.

In view of the disclosure provided herein, it is to be noted that the process conditions (e.g., reaction time, temperature and/or pressure, agitation or mixing rate, concentrations or molar ratios of starting components or reagents, etc.) may be determined or optimized by one of ordinary skill in the art, in order for example to optimize process efficiency or yield. For example, in one or more embodiments, the reaction is typically allowed to proceed, with optional mixing or agitation, for at least about 1 hour, about 2 hour, about 4 hours or more, and typically less than about 10 hours, about 8 hours or even about 6 hours, the reaction duration being for example between about 1 and about 10 hours, or about 2 and about 8 hours, or about 4 and about 6 hours. The present process may be carried out during this reaction period or duration at a temperature between about −20° C. and about 100° C., or between about −10° C. and about 75° C., or between about 0° C. and about 45 or 50° C., with higher reaction temperatures typically being used in combination with short reaction times and vice versa. The reaction may be carried out at any suitable atmosphere and/or pressure; for example an ambient atmosphere and/or standard atmospheric pressure may be used for the reaction. Alternatively, the reaction may be carried out in an inert atmosphere, such as in a nitrogen atmosphere, and/or the reaction may be carried out under increased or reduced (e.g., vacuum) pressure.

As previously noted, the starting concentration of each reagent or starting component in the reaction solution or mixture (e.g., the concentration of the starting compound, such as the starting dihydrosinomenine compound, the super acid, optional additional acids or anhydrides, etc.), and/or the ratio of one component to another, may be optimized using means generally known in the art to achieve the desired result (e.g., yield or purity of the fused, hetero-tetracyclic compound, such as the hydrocodone compound). Typically, however, the concentration of the starting compound (e.g., the starting dihydrosinomenine compound) may range from about 1% to about 20% (based on the total weight of the reaction solution or mixture), and in various embodiments may range from about 2% to about 18%, or from about 5% to about 15%. Similarly, the concentration of the super acid may range from about 5% to about 90% (based on the total weight of the reaction solution or mixture), and in various embodiments may range from about 10% to about 85%, from about 20% to about 80%, or even from about 30% to about 75%. When present, the concentration of the optional secondary acid may range from about 5% to about 90%, from about 10% to about 85%, from about 20% to about 80%; or from about 30% to about 75% (based on the total weight of the reaction mixture or solution), and/or the concentration of the optional anhydride may range from about 1% to about 20%, from about 2% to about 18%, or from about 5% to about 15% (based on the total weight of the reaction mixture or solution). Additionally, or alternatively, the molar ratio of the starting compound (e.g., the starting dihydrosinomenine compound) to the super acid may range from about 1:5 to about 1:200; and in various embodiments may range from about 1:10 to about 1:150, or from about 1:25 to about 1:100, while in alternative embodiments it may range from about 1:100 to about 1:200, from about 1:50 to about 1:150 m, or from about 1:10 to about 1:50; or any other suitable molar ratio.

Table 2, below, shows data as to the percent crude yield and percent purity of (+)-hydrocodone produced from 2H-sinomenine via furan ring closure reactions as described in the Examples hereinafter, with varying concentrations of reagents. The first column of Table 2 indicates which reaction conditions the ring closure reaction was run under, wherein the number in the column corresponds to one of the Examples described hereinafter. The reaction conditions thus correspond to those described in the corresponding Example, but wherein the relative equivalent of starting materials is as indicated in columns 2, 3 and 4. Columns 2, 3 and 4 show the equivalent of starting materials utilized in each particular reaction, where equivalent (eq) means the mole/mole ratio of that particular reagent relative to the starting material, e.g., 2H-sinomenine. Columns 5 and 6, respectively, show the percent crude yield and the percent purity of the (+)-hydrocodone thus produced.

TABLE 2

| Reaction conditions | $CF_3SO_3H$ | $(CF_3SO_2)_2O$ | $CH_3SO_3H$ | Crude Yield % | Purity % |
|---|---|---|---|---|---|
| 1 | 137 eq | 0 | 0 | 16 | 83.5 |
| 1 | 50 eq | 0 | 0 | 41 | 82 |
| 1 | 20 eq | 0 | 0 | 32 | 69 |
| 1 | 10 eq | 0 | 0 | 62 | 63 |
| 2 | 10 eq | 0 | 0 | 74 | 70 |
| 3 | 10 eq | 2 eq | 0 | 51 | 69.2 |
| 1 | 8 eq | 0 | 0 | 74 | 61 |
| 1 | 5 eq | 0 | 0 | 49 | 22 |
| 4 | 5 eq | 0 | 5 eq | 80 | 35.5 |

In this regard it is to be noted that the yield and/or purity of the desired reaction product may be improved or increase by, for example, optimizing process conditions (e.g., reaction time, temperature, reagent concentration or ratios, etc.). Accordingly, the data provided in Table 2 should not be viewed in a limit sense. For example, in various embodiments yield of the desired reaction product may be in the range of from about 15% to about 90%, based on the total weight of the reaction mixture or solution, and in particular may range from about 25% to about 85%, or from about 40% to about 75% (based on the total weight of the reaction mixture or solution). Additionally, or alternatively, the reaction product may be isolated from the reaction mixture or solution such that product ultimately having a purity of at least about 60%, and may optionally have a purity of at least about 70% or even about 80%.

As previously noted, suitable starting materials for the reactions detailed herein above may be obtained commercially, or alternatively may be prepared using means generally known in the art. For example, suitable starting compounds according to Formulas (I), (III), (V) or (VII), may be obtained commercially, for example from Aldrich, or may be synthesized from materials obtained from Aldrich and/or other chemical companies. Exemplary starting compounds include, but are not limited to the following:

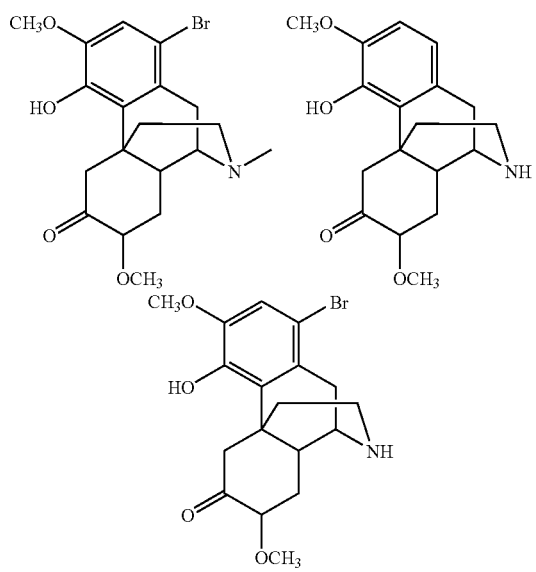

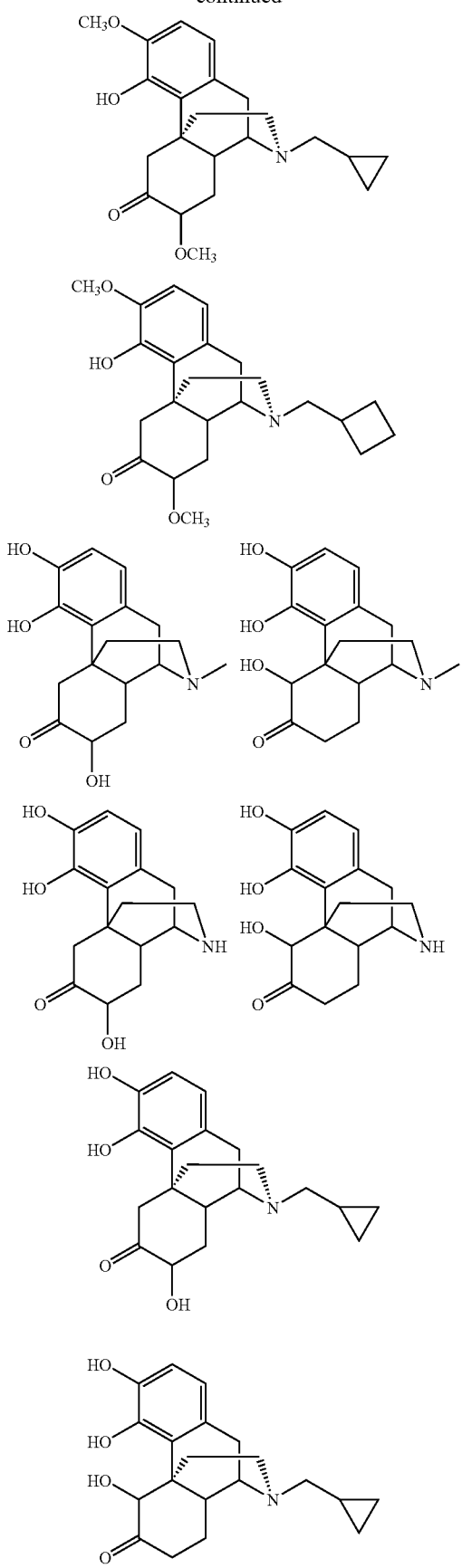

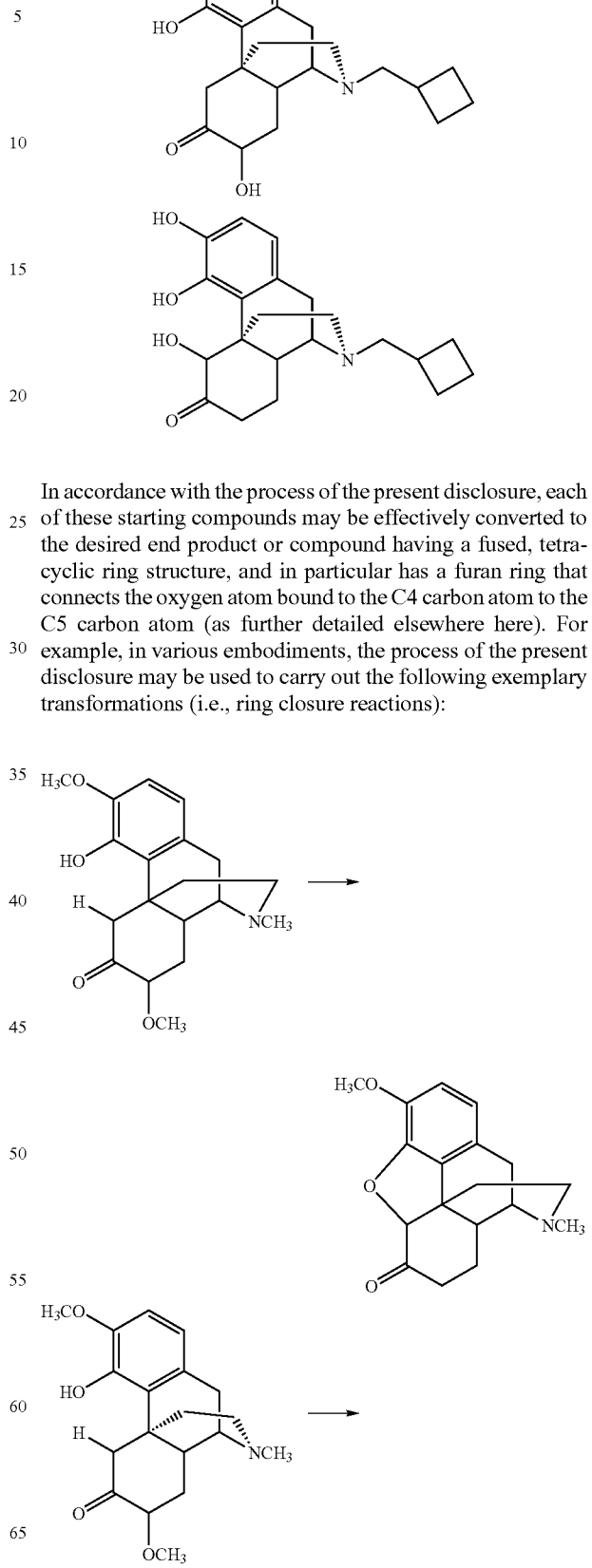

In accordance with the process of the present disclosure, each of these starting compounds may be effectively converted to the desired end product or compound having a fused, tetracyclic ring structure, and in particular has a furan ring that connects the oxygen atom bound to the C4 carbon atom to the C5 carbon atom (as further detailed elsewhere here). For example, in various embodiments, the process of the present disclosure may be used to carry out the following exemplary transformations (i.e., ring closure reactions):

-continued

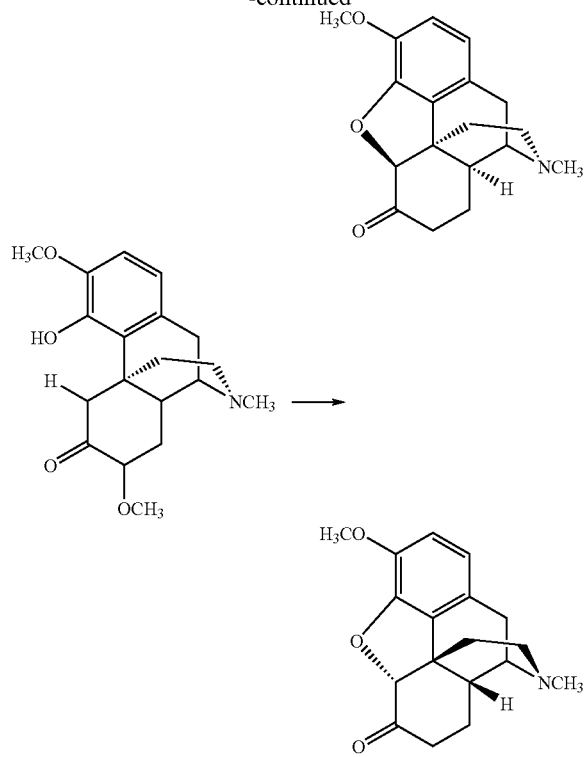

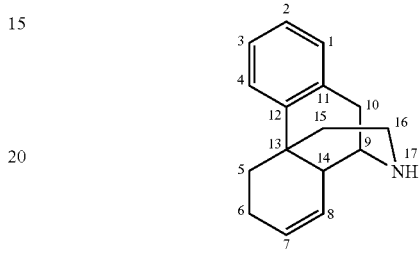

After the reaction of the present disclosure is completed (as determined, for example, by means generally known in the art, including for example the expiration of a desired reaction duration or period of time, and/or through the use of common analytical techniques, such as conventional chromatography techniques, to detect the presence of the reaction product or absence of starting components), the reaction may be stopped or quenched, also using means generally known in the art (e.g., by removing the reaction mixture or solution from any head source, by rapidly cooling the reaction mixture, and/or by the introduction of water). Once the reaction is complete, the reaction product may be isolated from the reaction mixture or solution using means generally known in the art. For example, in one particular embodiment, the reaction mixture may be subject to a pH adjustment by introduction of an appropriate type and quantity of base (e.g., to achieve a neutral or basic pH, the pH for example being in the range of about 8 to about 14, or about 8 to about 12, or about 8 to about 10), and then the reaction product may be isolated therefrom by means of solvent extraction, and/or by solvent removal (e.g., evaporation). Once isolated, the product may be subject to further purification techniques if needed (e.g., re-crystallization and/or washing with an appropriate solvent), and then dried.

Also as previously noted, the fused, hetero-tetracyclic compound that is the reaction product of the present disclosure (e.g., the hydrocodone compound) may be used directly, or alternatively it may be used as an intermediate reaction product and thus subjected to additional reaction techniques generally known in the art to prepare another product (e.g., another opiate, and in particular an unnatural, or a non-naturally occurring, (+)-opiate). For example, (+)-hydrocodone can be converted to (+)-hydromorphone by its reaction with $BBr_3$. (+)-Hydromorphone can be further converted to (+)-morphine by the method reported for the conversion of hydromorphone to morphine. In addition, pharmaceutically acceptable salts (e.g., sodium, potassium, calcium, etc.) of any of the compounds described herein are within the scope of this disclosure.

The compounds described herein may have a number of carbon atoms that have a (−) or (+) stereochemistry configuration, with respect to the rotation of polarized light. More specifically, the compounds described here may have a number of chiral centers, which may have an R or an S configuration. For ease of discussion, the ring atoms of the core hetero-tetracyclic structure referenced herein are numbered as follows:

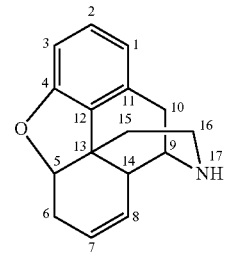

In the above structure, carbons 13, 14, and 9 are chiral centers. Accordingly, the configuration of a compound having the above structure, such as the starting compound of formulas I, III and V, as detailed above, may be RRR, RRS, RSR, RSS, SRR, SRS, SSR, or SSS with respect to C13, C14, and C9, respectively, provided that the C15 and the C16 atoms are both either on the alpha face of the molecule or the beta face of the molecule. In this context, in some embodiments, the stereochemistry of the C13, C14 and C9 carbons can and will vary without departing from the scope of the disclosure. In certain embodiments, the compounds within these formulas in the starting materials may be (+) or (−) enantiomers.

For a product compound of formulas II, IV and VI, as described above, carbons 5, 13, 14 and 9 may be chiral centers (and are in, for example, the structure provided below below). The stereochemistry of the C5, C13, C14, and C9 carbons can and will vary without departing from the scope of the disclosure. For example, the stereochemistry may be a RRRR, RRSR, RRRS, RRSS, RSRR, RSSR, RSRS, RSSS, SRRR, SRSR, SRRS, SRSS, SSRR, SSSR, SSRS or SSSS, with respect to C5, C13, C14 and C9, respectively, provided that the C15 and the C16 atoms are both either on the alpha face of the molecule or the beta face of the molecule.

Regardless of whether the fused, hetero-tetracyclic compound is to be used as a final product, or as an intermediate in the preparation of another opiate, it is to be noted that, once the desired reaction product is obtained, it may be formulated using means generally known in the art to obtain the desired pharmaceutical formulation or composition, for administration.

DEFINITIONS

As used herein, the following terms and phrases have the following general meanings.

The term "fused, tricyclic" or "fused, tetracyclic" generally refers to a compound that includes three or four, respectively, rings therein, and further wherein each of the rings in the compound share two ring atoms (e.g., carbon atoms or heteroatoms, as highlighted by the dashed-circles below) with one of the other rings.

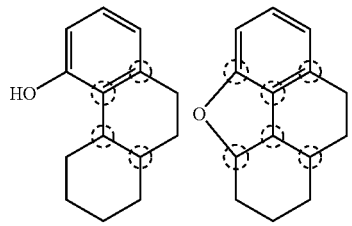

Additionally, the term "fused, hetero-tetracyclic" generally refers to a structure that includes four fused rings, at least one of which includes a heteroatom as a ring atom therein.

The terms "aryl" as used herein, alone or as part of another group, denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl groups.

The term 'halogen' or 'halo' as used herein alone or as part of another group generally refers to chlorine, bromine, fluorine and iodine.

The term 'acyl' as used herein alone or as part of another group generally refers to a moiety formed by removal of the hydroxy group from the group —COOH of an organic carboxylic acid, e.g., $R_xC(O)$—, wherein $R_x$ may be hydrocarbyl, or heterohydrocarbyl (e.g., hydrocarbyl-S, hydrocarbyl-N, hydrocarbyl-O, etc.), cylo, or heterocyclo.

The term 'hydrocarbyl' or 'hydrocarbon' as used herein describe organic compounds or radicals consisting exclusively of the elements carbon and hydrogen. These moieties include alkyl, alkenyl, alkynyl and aryl moieties. These moieties also include alkyl, alkenyl, alkynyl and aryl moieties substituted with other aliphatic or cyclic hydrocarbon groups such as alkaryl, alkenaryl and alkynaryl. Unless otherwise indicated, these moieties preferably comprise 1 to 20 carbon atoms.

The term 'substituted hydrocarbyl' or 'heterohydrocarbyl' refers to hydrocarbyl moieties that are substituted with at least one other moiety, and in particular one other atom other than carbon, including moieties in which a carbon chain atom is substituted with a hetero atom such as nitrogen, oxygen, silicon, phosphorous, boron, sulfur or a halogen atom. These substituents include halogen, heterocyclo, alkoxy, alkenoxy, aryloxy, hydroxy, protected hydroxy, acyl, acyloxy, nitro, amino, amido, nitro, cyano, ketals, acetals, esters and ethers.

The term 'heterocyclo' or 'heterocyclic' as used herein describe optionally substituted, fully saturated or unsaturated, monocyclic or bicyclic, aromatic or non-aromatic groups having at least one heteroatom in at least one ring, and preferably 5 or 6 atoms in each ring.

The term 'trialkylsilyl' refers to derivatives of the silyl group $R_3Si$—, wherein each of the three R groups are independently alkyl.

The term 'alkyl' as used herein refers to groups that contain up to 20 carbon atoms in the principle chain, but preferably refers to lower alkyl chains containing from 1 to 10, 1 to 8, or even 1 to 4 carbon atoms in the principal chain. These may be straight or branched chains, or cyclic, and include for example methyl, ethyl, propyl, isopropyl, butyl, pentyl, allyl, benzyl, hexyl and the like. Similarly, The term 'alkenyl' and "alkynyl" as used herein describe groups which contains up to 20 carbon atoms in the principle chain, and at least one carbon-carbon double bond (alkenyl) or triple bond (alkynyl), but preferably refers to lower alkyl chains containing from 2 to 10, 2 to 8, or even 2 to 4 carbon atoms in the principal chain. These may be straight or branched chains, or cyclic, and include for example ethenyl, ethynyl, propenyl, propynyl, etc.

The term "alkoxy" as used herein refers to an alkyl group as defined above that is combined with an oxygen atom in the principle chain (e.g., a chain having for example 1 to 10, 1 to 8 or even 1 to 4 carbon atoms and at least one oxygen atom in the principle chain, which serves for example as the point of attachment of the group to the remaining portion of the molecule of interest).

EXAMPLES

The following non-limiting examples are provided to further illustrate the present disclosure.

Example 1

Ring Closure Using Trifluoromethanesulfonic Acid

A solution of 1.1 grams of dihydrosinomenine in 5 ml chloroform was added dropwise into a cooled mixture of 5 grams trifluoromethanesulfonic acid and 7 ml chloroform in an ice bath. After finishing addition, the ice bath was removed, and the reaction solution was allowed to warm up to room temperature. After 5 hours, with continuous stirring, the reaction solution was poured into stirring ice water. The pH of the resulting mixture was adjusted to 12, with addition of 2.5 M potassium hydroxide aqueous solution. The product was then extracted with dichloromethane (3×50 ml). The combined organic phases were washed with 2.5 M potassium hydroxide aqueous solution (3×50 ml) and water (1×50 ml), dried over anhydrous magnesium sulfate, then filtered and evaporated to dryness to give 7 g of a light yellow solid containing 70% (+)-hydrocodone.

Example 2

Ring Closure Using Trifluoromethanesulfonic Acid at Room Temperature

A solution of 11 grams of dihydrosinomenine in 50 ml chloroform was added dropwise into a mixture of 50 grams trifluoromethanesulfonic acid and 70 ml chloroform at room temperature. The reaction mixture was stirred at room temperature for 5 hours, and then poured into stirring ice water. The pH of the resulting mixture was adjusted to 12 with 2.5 M potassium hydroxide. The product was extracted with dichloromethane (3×50 ml). The combined organic phases were washed with 2.5 M potassium hydroxide aqueous solution (2×30 ml) and water (1×50 ml), and then evaporated to dryness. The crude material thus obtained was then dissolved in a mixture of isopropanol, water and acetic acid. The product was precipitated from the solution by adjusting the pH to 12 with concentrated ammonia solution. The product was filtered and dried in vacuum at 60° C. overnight. This process yielded 6.2 grams of light yellow solid containing 85% (+)-hydrocodone.

Example 3

Ring Closure Using Mixture of Trifluoromethanesulfonic Acid and Trifluoromethanesulfonic Acid Anhydride A solution of 5 grams of trifluoromethanesulfonic acid and 1.12 ml trifluoromethanesulfonic anhydride was heated in an 86° C. water bath for 15 minutes. After cooling to room temperature, 7 ml chloroform was added. A solution of 1.1 g dihydrosinomenine in 5 ml chloroform was added dropwise to the mixture. The resulting reaction mixture was stirred at room temperature for five hours, and then poured into ice water. The pH of the resulting mixture was adjusted to 12 with 2.5 M potassium hydroxide aqueous solution. The reaction product was extracted with dichloromethane (3×50 ml). The combined organic phases were washed with 2.5 M potassium hydroxide aqueous solution (2×30 ml) and water (1×50 ml), dried over anhydrous magnesium sulfate, then filtered and evaporated to dryness to give 0.51 g of a light yellow solid containing 51% (+)-hydrocodone.

Example 4

Ring Closure Using Mixture of Trifluoromethanesulfonic Acid and Methanesulfonic Acid A solution of 1.1 grams of dihydrosinomenine in 5 ml chloroform was added dropwise to a mixture of 2.5 grams of trifluoromethanesulfonic acid, 1.08 ml methanesulfonic acid and 7 ml chloroform at room temperature. The mixture was stirred at room temperature for five hours, and then poured into stirring ice water. The pH of the resulting mixture was adjusted to 14 with 2.5 M potassium hydroxide. The reaction product was extracted with dichloromethane (3×50 ml). The combined organic phases were washed with 2.5 M potassium hydroxide aqueous solution (2×30 ml) and water (1×50 ml), dried over anhydrous magnesium sulfate, then filtered and evaporated to dryness to give a green-yellow solid containing (+)-hydrocodone.

When introducing elements of the present disclosure or the embodiment(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several feature or objects of the disclosure are achieved and other advantageous results attained.

As various changes could be made in the above compositions, products, and methods (including concentrations of reagents, process conditions, etc.) without departing from the scope of the present disclosure, it is intended that all matter contained in the above description shall be interpreted as illustrative and not in a limiting sense.

What is claimed is:
1. A process for carrying out a furan ring closure reaction to transform a compound of Formula (III) to a compound of Formula (IV):

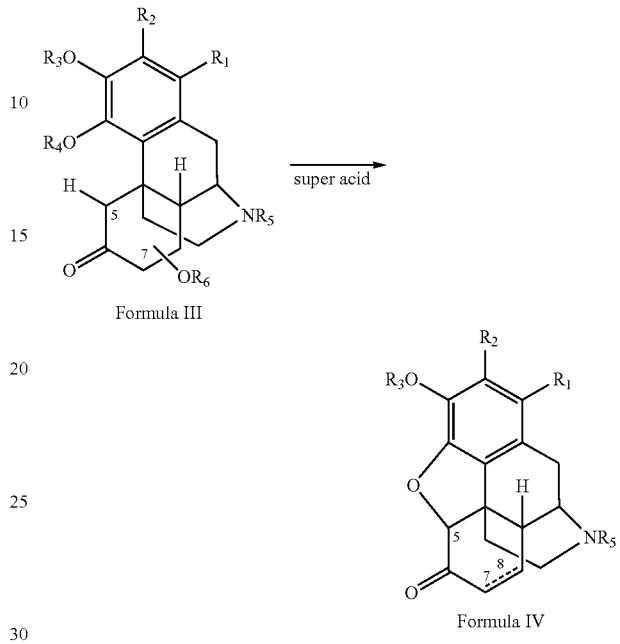

Formula III

Formula IV wherein:
$R_1$ and $R_2$ are independently selected from the group consisting of hydrogen, halogen, hydroxy, alkoxy, cyano, hydrocarbyl, substituted hydrocarbyl and $NR_cR_d$, where each of $R_c$ and $R_d$ are independently selected from the group consisting of hydrogen, hydroxy and hydrocarbyl;
$R_3$ and $R_5$ are independently selected from the group consisting of hydrogen, hydrocarbyl and substituted hydrocarbyl;
$R_4$ is selected from the group consisting of hydrogen, acyl, trialkylsilyl, tertiary-alkyl, aryl-substituted methyl, and alkoxy-carbonyl;
$R_6$ is a substituent at C5 or C7 and is selected from hydrogen, alkyl, and acyl; and, the dashed bond between carbon atoms C7 and C8 indicates the optional presence of a carbon-carbon double bond;
the process comprising contacting the compound of formula (III) with a super acid under process conditions suitable for forming a bond between the oxygen atom of the —$OR_4$ substituent and the C5 carbon atom to form a furan ring.

2. The process of claim 1, wherein the super acid is selected from the group consisting of $CF_3SO_3H$ (trifluoromethanesulfonic acid), $HBF_4$ (tetrafluoroboric acid), $HPF_6$ (fluorophosphoric acid), $FSO_3H$ (fluorosulfuric acid), $HSbF_6$ (fluoroantimonic acid), $FP(O)(OH)_2$ (fluorophosphoric acid), and combinations thereof.

3. The process of claim 1, wherein the super acid and the compound of Formula (III) are contacted in a reaction mixture further comprising an aprotic solvent.

4. The process of claim 3, wherein the aprotic solvent is selected from the group consisting of chloroform, dichloromethane, chlorobenzene, toluene, dichloroethane, tetrahydrofuran, diethyl ether, acetonitrile, and combinations thereof.

5. The process of claim 1, wherein the super acid is formed in situ.

6. The process of claim 5, wherein the super acid is formed in situ by reacting water or methanol with an anhydride of the super acid.

7. The process of claim 1, wherein the process further comprises contacting the compound of Formula (III) with an acid that is not a super acid.

8. The process of claim 7, wherein the acid that is not a super acid is selected from the group consisting of MeSO$_3$H, CH$_3$C$_6$H$_4$SO$_3$H, H$_3$PO$_4$ and CF$_3$CO$_2$H, and combinations thereof.

9. The process of claim 1, wherein $R_1$, $R_2$ and $R_4$ are hydrogen.

10. The process of claim 9, wherein $R_3$ and $R_5$ are methyl.

11. The process of claim 1, wherein $R_3$ and $R_5$ are hydrogen.

12. The process of claim 1, wherein $R_3$ is methyl and $R_5$ is hydrogen.

13. The process of claim 1, wherein $R_1$ and $R_4$ are hydrogen; $R_2$ is bromine; and $R_3$, $R_5$ and $R_6$ are methyl.

14. The process of claim 1, wherein $R_1$, $R_2$ and $R_4$ are hydrogen; $R_3$ and $R_6$ are methyl; and $R_5$ is cyclopropylmethyl.

15. The process of claim 1, wherein $R_1$, $R_2$, $R_4$ and $R_5$ are hydrogen and $R_3$ and $R_6$ are methyl.

16. The process of claim 1, wherein $R_1$, $R_2$, $R_3$, $R_4$ and $R_6$ are hydrogen; and $R_5$ is methyl.

17. The process of claim 1, wherein $R_1$, $R_2$ and $R_4$ are hydrogen and $R_3$, $R_5$ and $R_6$ are methyl.

18. The process of claim 17, wherein the compound of Formula (III) is (+)-hydrocodone.

19. The process of claim 1, wherein the resulting mixture of the compound of Formula (III) and the super acid is agitated for between about 2 and about 8 hours, or between about 4 and about 6 hours.

20. The process of claim 1, wherein the resulting mixture of the compound of Formula (III) and the super acid is maintained at a temperature between about −20° C. and about 100° C., or between about 0° C. and about 45° C.

21. The process of claim 1, wherein the compound of Formula III and the compound of Formula IV have the following structures:

wherein $R_6$ is H or CH$_3$.

22. The process of claim 1, wherein the compound of Formula III and the compound of Formula IV have the following structures:

wherein $R_6$ is H or CH$_3$.

23. A process for making a compound of Formula (VI):

Formula V

Formula VI wherein:

$R_1$ and $R_2$ are independently selected from the group consisting of hydrogen, halogen, alkoxy, cyano, hydrocarbyl, substituted hydrocarbyl and NR$_c$R$_d$, wherein each of R$_c$ and R$_d$ are independently selected from the group consisting of hydrogen hydroxy and hydrocarbyl;

$R_3$ and $R_5$ are independently selected from the group consisting of hydrogen, hydrocarbyl and substituted hydrocarbyl;

$R_4$ is selected from the group consisting of hydrogen, acyl, trialkylsilyl, tertiary-alkyl, aryl-substituted methyl and alkoxy carbonyl; and, $R_6$ is a substituent at C5 or C7 and is selected from H or $CH_3$;

the process comprising contacting a compound of Formula (V) with a super acid under process conditions suitable for forming a bond between the oxygen atom of the $-OR_4$ substituent and the C5 carbon atom to form a furan ring.

24. The process of claim 23, wherein $R_1$, $R_2$ and $R_4$ are H, and $R_3$ and $R_5$ are $CH_3$.

* * * * *